US00PP30305P2

(12) United States Plant Patent
Korlipara

(10) Patent No.: US PP30,305 P2
(45) Date of Patent: Mar. 19, 2019

(54) ***ECHINACEA* PLANT NAMED 'TNECHPDF'**

(50) Latin Name: ***Echinacea* spp.**
Varietal Denomination: TNECHPDF

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,499

(22) Filed: Mar. 7, 2018

(51) Int. Cl.
*A01H 5/02* (2018.01)

(52) U.S. Cl.
USPC ..... Plt./428

(58) Field of Classification Search
USPC ..... Plt./428
See application file for complete search history.

*Primary Examiner* — Annette H Para
(74) *Attorney, Agent, or Firm* — Klarquist Sparkman, LLP

(57) ABSTRACT

A new and distinct *Echinacea* plant named 'TNECHPDF' characterized by red purple-colored ray florets, enlarged red purple-colored disc florets forming an anemone-type inflorescence, a multicrown, dwarf habit with upright strong stems, and excellent vigor.

1 Drawing Sheet

Botanical denomination: *Echinacea* spp.
Variety designation: 'TNECHPDF'.
Trademark designation: Paso Doble™ Fuchsia

BACKGROUND OF THE INVENTION

The present invention relates to a new and distinct cultivar of *Echinacea* and given the cultivar name 'TNECHPDF'. *Echinacea* is in the family Asteraceae. The new cultivar is part of a planned breeding program for a landscape series with compact habits and profuse double inflorescences. The exact parents of this selection are unknown, unnamed, proprietary interspecific hybrids bred from *Echinacea paradoxa, Echinacea purpurea*, and *Echinacea tennesseensis.*

Compared to *Echinacea* 'TNECHCMR', U.S. Plant Pat. No. 28,749, the new cultivar is more upright, with shorter peduncles, and with inflorescences that red purple rather than dark raspberry colored.

Compared to *Echinacea* 'Cranberry Cupcake' (U.S. Plant Pat. No. 23,020), the new cultivar is shorter, with inflorescences that dark raspberry-colored rather than rose pink.

This new *Echinacea* cultivar is uniquely distinguished by:

1. red purple colored ray florets,
2. enlarged red purple disc florets forming an anemone-type inflorescence,
3. a multicrown, dwarf habit with upright strong stems, and
4. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a nine-month-old *Echinacea* 'TNECHPDF' growing in the trial field in full sun in late July in Canby, Oreg.

DETAILED PLANT DESCRIPTION

The following is a detailed description of the new *Echinacea* cultivar based on observations of 8-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition.

Plant:

*Type.*—Herbaceous perennial.
*Hardiness.*—USDA Zones 4 to 9.
*Size.*—Grows to 39 cm wide and 46 cm tall to top of inflorescences.
*Form.*—Basal clump, with about 14 stems from the base.
*Vigor.*—Excellent.
*Roots.*—Fibrous, with many downward growing and few laterals, ivory in color, Yellow White 158D, roots develop easily from cuttings from the crown.

Leaf (stem):

*Type.*—Simple.
*Shape.*—Lanceolate.
*Arrangement.*—Alternate.
*Blade size.*—Grows to 9.5 cm long and 4.3 cm wide.
*Margins.*—Sparsely serrate to entire.
*Apex.*—Acuminate.
*Base.*—Attenuate.

*Surface texture*.—Strigose on both sides.

*Venation*.—Pinnate, Yellow Green 145C on both sides.

*Color*.—Topside Green 137A, bottom side closest to Yellow Green 147B.

*Petiole description*.—Clasping, grows to 11 cm long and 4 mm wide, scabrous, narrow leafy edges, both sides Yellow Green 145C, topside lightly tinted Greyed Purple 187A.

Inflorescence:

*Type*.—Composite on terminal stalked heads.

*Flowering stem*.—Grows to 44 cm tall from the base of the plant to the terminal inflorescence; unbranched to branched, with 1 to 4 inflorescences per stem; diameter growing to 5 mm wide near the inflorescence; strigose; Yellow Green 146C in shade, tinted 187A in sun.

*Size*.—Grows to 8 cm wide and 6 cm deep as disc enlarges.

*Form*.—Ray florets held slightly down, reflexing more in older inflorescences, mature disc is conic.

*Immature inflorescence* (*bud*).—2 cm wide and 1.3 cm deep, ray florets held upright rolled up so only the back color shows, Greyed Purple 187C, disc color Greyed Brown 199A.

*Ray florets*.—Without pistil or stamen, to 27 in number, 40 mm long and 13 mm wide, oblanceolate with the tip two-to three-toothed (each acute), main two teeth cut 3 mm to 10 mm deep, entire margins, base attenuate, glabrous on both sides; newly fully open florets topside closest to Red Purple 60B, bottom side Greyed Purple 186B; florets darken to topside Red Purple 64A, bottom side Red Purple 70A.

*Disc*.—Flat becoming conic, becoming to 45 mm deep and 60 mm wide with maturity, overall color Red Purple 64A.

*Disc florets*.—To about 500 in number, each with 1 pistil and 4 stamen, grow to 25 mm long and 8 mm wide, each with one persistent bract (9 mm long with the top 1 mm colored Greyed Purple 187A to 2 mm Orange 24A to 4 mm Yellow Green 148D blending to White NN155B); showy 5-lobed corollas to 21 mm long and 10 mm wide, tubular on the bottom with the lobes spread out like a fan, glabrous on both sides; back side Greyed Purple 187A on tips, to Red Purple 70B on lobes lightening to White NN155B at base, inside color Greyed Purple 187A on tips to Red Purple 71A on lobes lightening to 64C at base; pistil 10 mm long, ovary 4 mm long, White NN155A, style 5 mm long Red Purple 72C, 2-branched stigma spreading 3 mm wide, Greyed Purple 187A; stamen 4.5 mm long and thread-like, anthers 2 mm long and Greyed Brown N199A, filaments 2.5 mm long, White 155A, pollen none.

*Involucral bracts*.—In 4 leafy series, area grows to 32 mm wide and 10 mm deep, lobes lanceolate in shape, reflexed, grow to 10 mm long and 3 mm wide, Green 137A, margins strigose, tip acute, strigose on both sides.

*Receptacle*.—Grows to 13 mm wide and 16 mm deep, White NN155B.

*Bloom period*.—June through October in Canby, Oreg.

*Fragrance*.—Slight.

*Lastingness*.—Each inflorescence lasts about two weeks in Canby, Oreg.

Seeds: None.

*Fertility*.—None.

Disease and pests: No pests or diseases have been observed on plants grown under commercial conditions in Canby, Oreg. No resistances are known.

I claim:

1. A new and distinct *Echinacea* plant as herein illustrated and described.

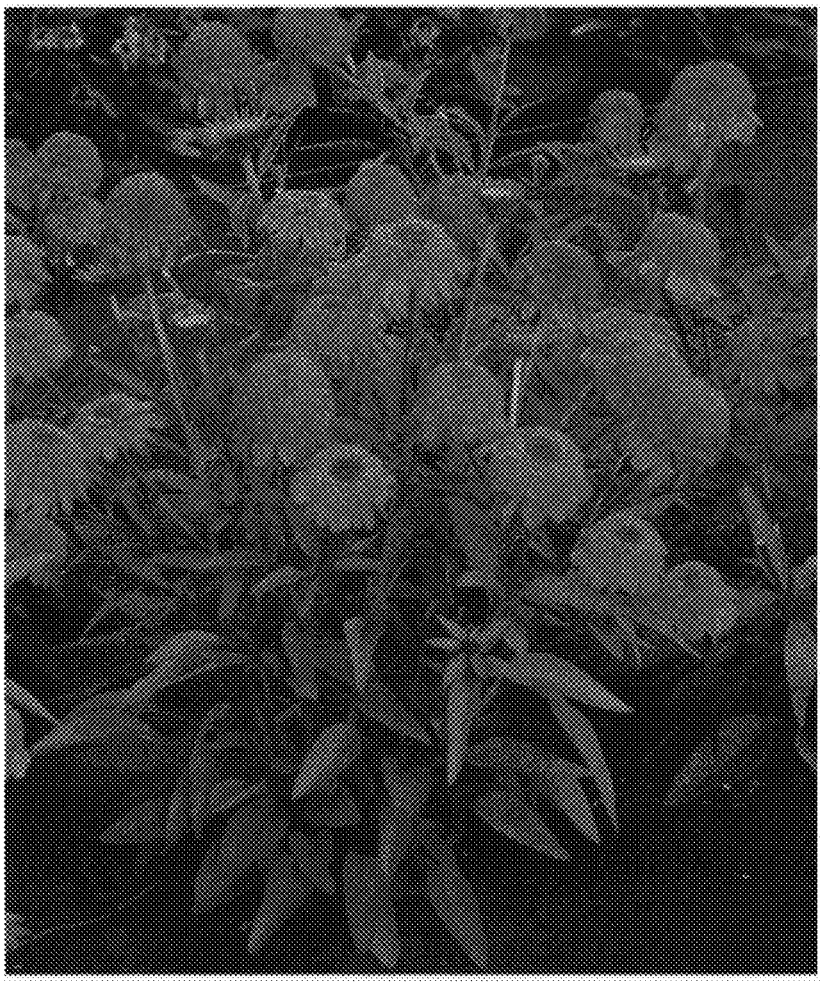

* * * * *